United States Patent [19]

Lary

[11] Patent Number: 4,548,601

[45] Date of Patent: Oct. 22, 1985

[54] PREPACKAGED, INJECTABLE PHARMACEUTICAL AND HYPODERMIC NEEDLE COMBINATION

[76] Inventor: Banning G. Lary, 6225 S.W. 117 Terrace, Miami, Fla. 33156

[21] Appl. No.: 597,939

[22] Filed: Apr. 9, 1984

[51] Int. Cl.[4] .............................. A61M 5/00
[52] U.S. Cl. ............................ 604/204; 604/212
[58] Field of Search ............. 604/214, 212, 204, 90, 604/201

[56] References Cited

U.S. PATENT DOCUMENTS

| | | | |
|---|---|---|---|
| 2,618,263 | 11/1952 | Lakso et al. | 604/214 |
| 2,696,213 | 12/1954 | Smith | 604/214 X |
| 2,771,879 | 11/1956 | Salisbury, Jr. | 604/214 |
| 4,059,109 | 11/1977 | Tischlinger | 604/90 |

Primary Examiner—John D. Yasko
Attorney, Agent, or Firm—Ernest H. Schmidt

[57] ABSTRACT

A prepackaged, injectable pharmaceutical hypodermic needle has semi-rigid outer container, supported within which is a substantially non-resilient inner container containing a pre-measured dose of the pharmaceutical. A cannula extending through and fixed with respect to the outer container is adapted to pierce the inner container for injection of the pharmaceutical upon manual collapsing or squeezing of the outer container. Air flow openings in the outer container permit the flow of air into the cavity between the inner and outer containers upon manual release during successive manual compression or squeezing operations, thereby obviating the possibility of negative air pressure being exerted upon the inner container.

6 Claims, 7 Drawing Figures

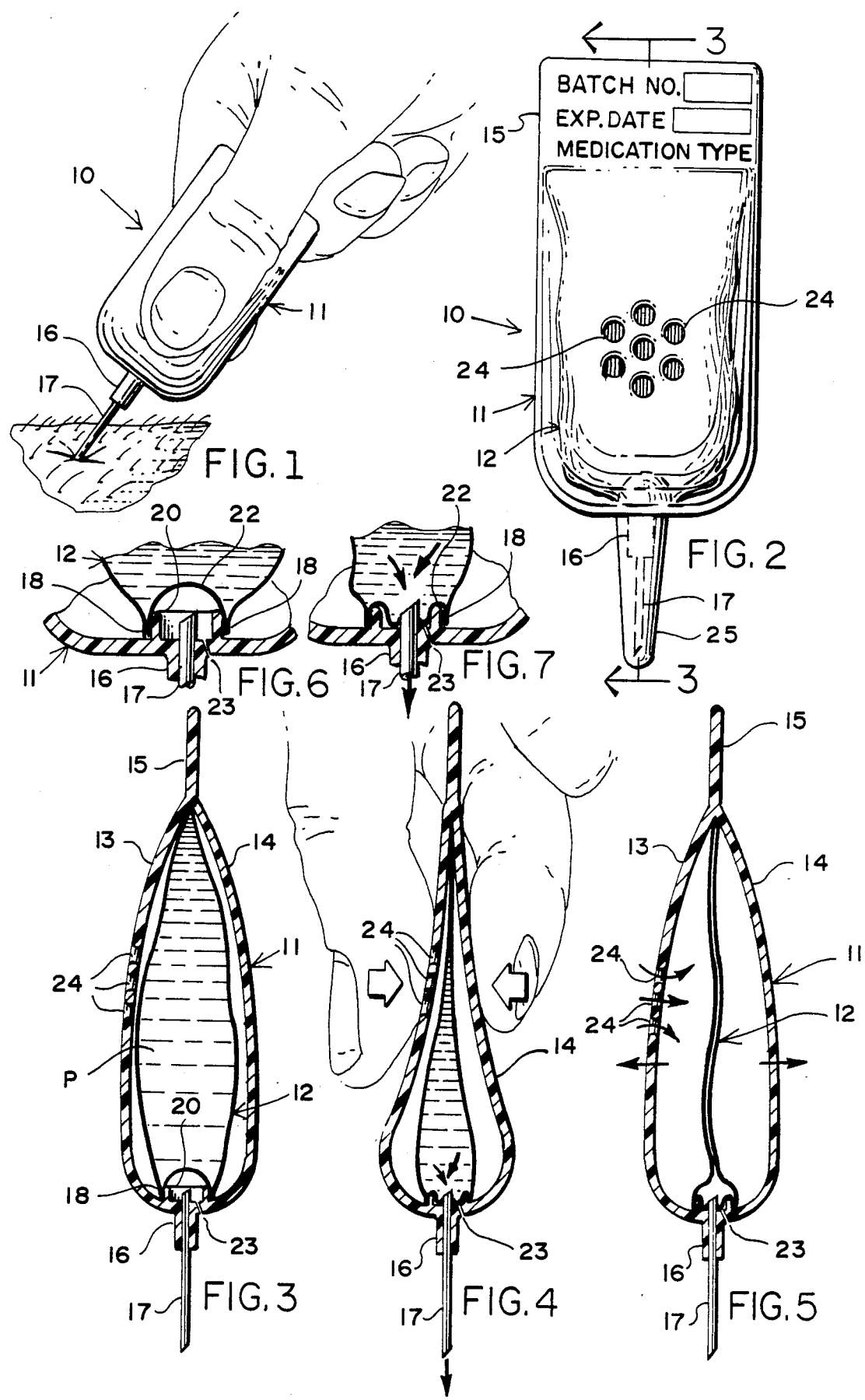

PREPACKAGED, INJECTABLE PHARMACEUTICAL AND HYPODERMIC NEEDLE COMBINATION

BACKGROUND OF THE INVENTION

In medical practice, it is often necessary to administer medication either subcutaneously or intravenously under emergency conditions. For this purpose, pre-loaded, disposable medicinal syringes have heretofore been devised which permit the injection of a pre-measured medicinal or pharmaceutical dose. U.S. Pat. No. 4,410,323 issued Oct. 18, 1983 to HODASH, et al, describes a pre-dosed disposable syringe of this type wherein the medication is contained within a hollow, flexible member which acts as a syringe upon its manual compression for injection through the usual cannula. In such known pre-dosed disposable syringes, the resiliant container syringe member is of such thickness and rigidity that it cannot be fully collapsed about the inwardly-projecting end of the cannula, so as to provide for expression or injection of the entire dose. If the pre-measured dose to be injected is comparatively small, as may be the case in potent injectables, significant under-dosing may result.

SUMMARY OF THE INVENTION

The principal object of my invention is to provide a prepackaged, injectable pharmaceutical and hypodermic needle combination which obviates the deficiencies of such devices heretofore devised.

A more particular object of my invention is to provide a prepackaged or pre-dosed pharmaceutical injection syringe device of the character described, wherein the injectable medication is contained within a substantially non-resiliant, highly flexible sack or inner container which is indirectly compressed, pneumatically, by means of a resiliant, comparatively rigid outer container. Manual collapsing pressure or squeezing of the outer container serves, in successive operations, to completely discharge the contents of the inner container through a cannula, thereby injecting its full dose.

Another object is to provide an injection device of the above nature which can be fabricated economically by molding of synthetic plastic materials, and in which the pharmaceutical to be injected remains hermetically sealed in its inner container until ready for injection.

Other objects, features and advantages of the invention will be apparent from the following description when read with reference to the accompanying drawings.

BRIEF DESCRIPTION OF THE DRAWINGS

In the drawings, wherein like reference numerals denote corresponding parts throughout the several views:

FIG. 1 illustrates a prepackaged, injectable pharmaceutical and hypodermic needle combination in use;

FIG. 2 is a front elevational view of the device, shown separately;

FIG. 3 is a vertical cross-sectional view taken along the plane indicated at 3—3 of FIG. 2 in the direction of the arrows;

FIG. 4 is a cross-sectional view similar to that of FIG. 3, but illustrating use of the device in manually expressing the contained pharmaceutical through the hollow needle or cannula for injection;

FIG. 5 is a cross-sectional view similar to that of FIG. 3, illustrating how the outer container returns to its original shape after the pharmaceutical has been injected;

FIG. 6 is a fragmentary enlargement of the lower portion of FIG. 3, where the cannula projects through the outer container, and;

FIG. 7 is a fragmentary enlargement of the lower portion of FIG. 4, illustrating how the internal, pharmaceutical containing sack is pierced for ejection of its contents.

Referring now in detail to the drawings, reference numeral 10 in FIGS. 1 and 2 illustrates a preferred form of prepackaged injectable pharmaceutical and hypodermic needle combination embodying the invention. With further reference to FIG. 3 it comprises, generally, a substantially rectangular, semi-rigid outer container 11 fully supported within which is a relatively flexible, impervious, inner container or sack 12 filled with a measured dose of a particular liquid pharmaceutical P to be hypodermically or intravenously injected.

As best illustrated in FIGS. 2 and 3, the outer container 12 is preferably fabricated by molding of a tough synthetic plastic material such as polypropylene, with sufficient wall thickness as normally to retain its elongated teardrop shape in longitudinal cross-section. The opposed sidewalls 13, 14 of the outer container 11 merge at their upper ends into an integrally-molded, rectangular tag portion 15, which will preferably be imprinted or otherwise impressed with identifying indicia of the pharmaceutical contents, such as the batch number, expiration date and medication type. The lower end of the semi-rigid outer container 11 has integrally molded therewith, at a central position therealong, a cylindrical boss or projection 16 through which a cannula 17 extends, being coaxally molded in place and hermetically sealed thereat. The inner container or sack 12, which is comparatively thin-walled, and also preferably fabricated of a tough, synthetic material, impermeable with respect to the pharmaceutical or liquid medication to be injected, is comparatively non-resilliant so that when collapsed in the manner hereinafter described, it has no tendency to assume its original shape. The upper end of the inner container or sack 12 is secured along the upper end of the cavity within the outer container 11 by having its marginal upper end portion integrally molded within a lower marginal portion of the outer container tag portion 15.

A lower end portion of the inner container or sack 12, illustrated at 18 in FIGS. 3 and 6, is heat-welded or otherwise peripherally secured to the outer wall of an annular projection 20 integrally formed within the outer container 11 in concentric disposition with respect to the inwardly-projecting portion of the cannula 17. The lower end of the inner container 12 is so attached as to leave a circular bottom wall portion 22 thereof looped over the inner end of the cannula, (see FIG. 6). As further illustrated in FIG. 6, a small vent hole 23 extends through the bottom of the outer container 11, near the boss 16 and closely adjacent to the inwardly-projecting end of the cannula 17, for the purpose hereinafter appearing. As best illustrated in FIGS. 2 and 3, the sidewall 13 of the outer container 11 is provided with a plurality of centrally located through openings 24, for the purpose hereinafter described. As illustrated in FIG. 2, the outwardly projecting cannula 17 and its associated projection or boss 16 will be protected against contamination by a cap 25 received over and retained in place by friction fit over said boss.

In use, the protective cap 25 will first be removed, after which the prepackaged injectable pharmaceutical and hypodermic needle combination 10 will be grasped between the thumb and forefinger as illustrated in FIG. 1 so that the thumb covers the sidewall through openings 24. The patient's site of injection will then be appropriately pierced by the cannula 17, as further illustrated in FIG. 1, after which, as illustrated in FIG. 4, the container sides will be pressed together to increase its internal air pressure and thereby pneumatically collapse the inner container or pharmaceutical sack 12. The pressure thus applied to the inner container forces the bottom wall loop portion 22 thereof down over the inner, sharp-pointed end of the cannula 17, whereupon it is pierced to permit flow under pressure through said cannula to the site of injection, as indicated by the arrows in FIG. 4. The small vent hole 23 serves to vent the small amount of air under the loop portion 22 of the sack 12 at this time. After partial injection has thus been achieved, uncovering some of the through openings 24 while at the same time releasing any substantial pressure against the outer container sides will allow said outer container to spring back to its normal expanded shape, with air replacing the volume of medication injected. The flexible nature of the circular bottom wall loop portion 22 of the inner container or sack 12 is such that after the cannula is pierced, it remains in abutting relation against the inside of the vent hole 23, thereby minimizing any possibility of reverse air flow upon release of compressional pressure against the outer container sidewalls. In this connection it is to be noted that the sidewall openings 24 are so large that upon being uncovered just prior to manual release, substantially no negative air pressure results within the outer container 11. A check valve protecting against reverse air flow through the vent opening 23 is therefore not ordinarily required. It is to be understood, however, that if required in any particular embodiment of the invention, the vent opening 23 could be provided with a check valve, in the form of a resiliantly retained flap or ball, for example. Upon next squeezing the sides of the outer container together again, while covering the through openings 24 with the thumb, the internal air pressure thereby resulting serves to pneumatically collapse inner container or sack 12, as illustrated in FIG. 5, so that substantially the entire quantity or dose of the medication is expressed. This can usually be done within 2 or 3 rapidly successive manual squeezing operations of the device.

While I have illustrated and described herein only one form in which my invention can conveniently be embodied in practice, it is to be understood that this embodiment is presented by way of example only and not in a limiting sense. The invention, in brief, comprises all the embodiments and modifications coming within the scope and spirit of the following claims.

What I claim as new and desire to secure by Letters Patent is:

1. A prepackaged, injectable pharmaceutical hypodermic needle combination comprising a semi-rigid outer container, a relatively flexible, substantially non-resiliant inner container supported within said outer container and fixed relative thereto at one end of said outer container, a cannula extending through said outer container at said relatively fixed end thereof, said outer container being comparatively resiliant so as to resume its original shape after being manually collapsed, a premeasured dose of an injectable pharmaceutical contained within said inner container, air passage means in said outer container for permitting the flow of air into the cavity between said inner and outer containers, means for communicatively interconnecting the interior of said inner container with the inwardly-extending end of said cannula, said air passage means comprising an opening in one of the side walls of said outer container, said opening being adapted for closure and sealing off by convering with the thumb upon manual squeezing of said outer container in an injecting procedure whereby, upon successive squeezing operations of said outer container during an injecting procedure said inner container will become completely collapsed by pneumatic pressure to fully express the contained pharmaceutical being injected.

2. A prepackaged, injectable pharmaceutical hypodermic needle combination as defined in claim 1, wherein said interconnecting means comprises a sharp point at the inner end of said cannula, an outer wall portion of said inner container normally being disposed in spaced relation with respect to said sharp point so as to be pierced by said cannula upon the exertion of pressurized air against the outside of said inner container.

3. A prepackaged, injectable pharmaceutical hypodermic needle combination as defined in claim 2 wherein said communicatively interconnecting means comprises an internal annular projection integrally formed within said inner container at said relatively fixed end thereof, said cannula extending coaxially through said annular projection, said outer wall portion of said inner container being peripherally attached to the outside of said annular projection and being hermetically sealed thereat, and a vent opening communicating between the outside of said outer container and the interior of said annular projection.

4. A prepackaged, injectable pharmaceutical hypodermic needle combination as defined in claim 1 wherein said inner and outer containers are fabricated of moldable synthetic plastic materials, and wherein the other end of said inner container is fixed to the other end of said outer container.

5. A prepackaged, injectable pharmaceutical hypodermic needle combination as defined in claim 4 wherein said other end of said outer container is integrally molded with a tag portion for the application of indicia relating to the pharmaceutical contained.

6. A prepackaged, injectable pharmaceutical hypodermic needle combination as defined in claim 3 wherein said outer wall portion of said inner container is defined by a circular loop over said pointed end, said circular loop being of such size as to permit its passing down into close-fitting engagement within the annular recess between said inwardly-projecting end of said cannula and said annular projection upon the force of injection being applied to said inner container, whereby said vent opening will be abuttingly sealed off against the re-entry of ambient air.

* * * * *